United States Patent [19]

Bryant et al.

[11] 4,213,702
[45] Jul. 22, 1980

[54] GLASS INSPECTION METHOD AND APPARATUS

[75] Inventors: Nelson Bryant, Ithaca; Rudy Hoppe, Valois, both of N.Y.

[73] Assignee: Powers Manufacturing, Inc, Elmira, N.Y.

[21] Appl. No.: 948,180

[22] Filed: Oct. 2, 1978

[51] Int. Cl.² .................................. G01N 21/32
[52] U.S. Cl. ........................ 356/239; 250/223 B; 250/224
[58] Field of Search .............. 356/237, 239, 240; 250/223 B, 224

[56] References Cited

U.S. PATENT DOCUMENTS

| 3,283,162 | 11/1966 | Quittner | 250/572 |
| 3,358,552 | 12/1967 | Schneider | 358/435 |
| 3,533,704 | 10/1970 | Krenmayr | 250/223 B |
| 3,955,179 | 5/1976 | Planke | 250/223 B |

FOREIGN PATENT DOCUMENTS 1061298  3/1967  United Kingdom .
1133339 11/1968  United Kingdom .

*Primary Examiner*—John K. Corbin
*Assistant Examiner*—Bruce Y. Arnold
*Attorney, Agent, or Firm*—Seidel, Gonda, Goldhammer & Panitch

[57] ABSTRACT

A region of a glass bottle is inspected for flaws or checks by scanning the region with a light beam. The passage of a flaw or check through the beam causes a fluctuation in the intensity of the light beam at two spaced apart locations. At each location, a sensor senses the fluctuation in beam intensity caused by the flaw or check. A difference amplifier generates a difference signal based on the sequential detection of the fluctuation in intensity of the light beam at the two locations. The difference signal is rectified and inverted. The inverted difference signal is rectified and combined with the rectified difference signal to produce a combined signal. If the combined signal exceeds a predetermined threshold value within a predetermined time interval, a reject signal is generated to operate a mechanism which removes the bottle by conventional means.

5 Claims, 5 Drawing Figures

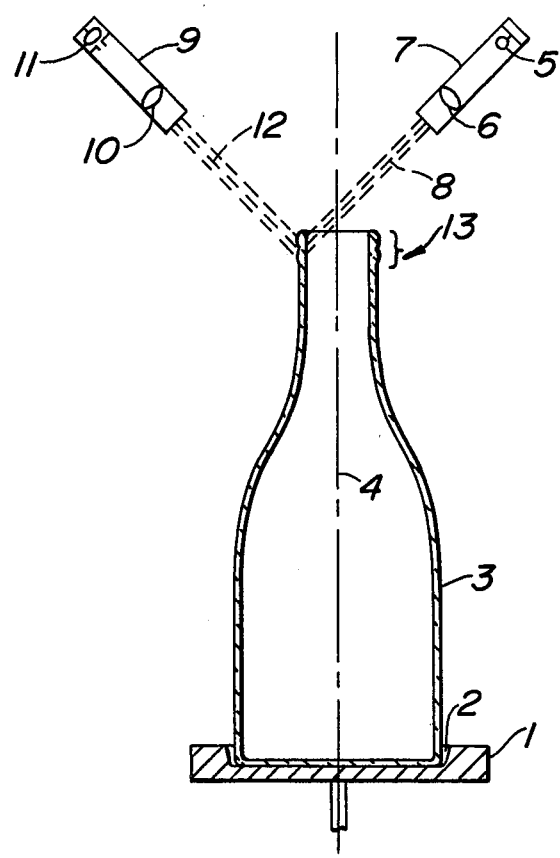
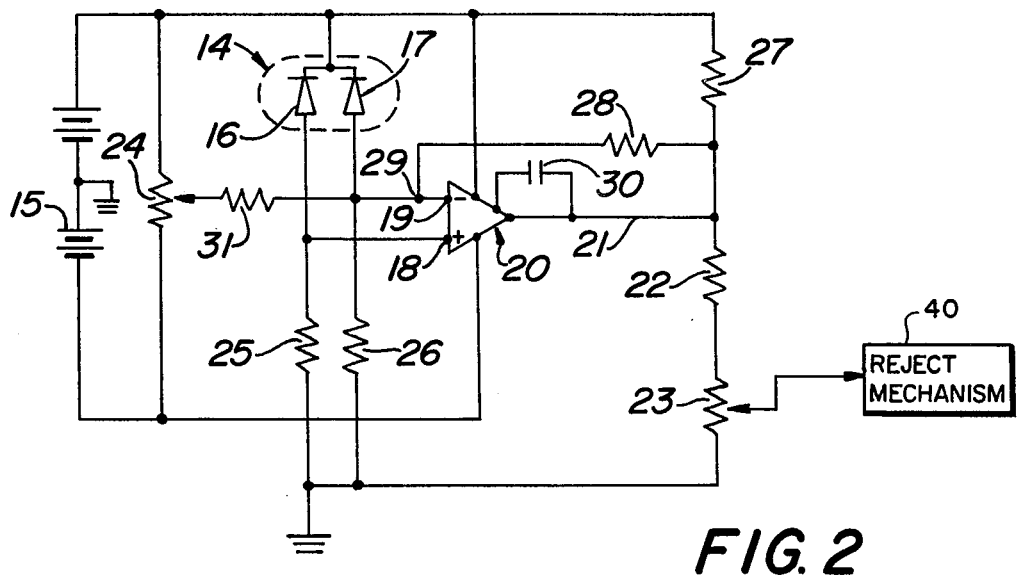
FIG. 1
FIG. 2

OUTPUT 21

INPUT 70

OUTPUT 78

MISSED DETECTION

GLASS INSPECTION METHOD AND APPARATUS

DISCLOSURE

This invention relates to apparatus for detecting cracks (often called checks) or similar flaws in a moving glass object, by which is to be understood an object moving relatively to the apparatus. The glass object or the apparatus may additionally be moving relatively to the environment. Thus, a stationary apparatus inspecting a rotating glass bottle, and an oscillatory apparatus which makes transverse inspection passes across an advancing sheet of float glass, are both within the scope of the invention.

Cracks or checks can appear in manufactured objects of glass shortly after molding or forming, and while the objects are still quite hot. It is desirable to reject such defective objects at an early stage in manufacture, and recycle the glass.

For this purpose, it is known to use apparatus comprising a visible or ultraviolet light beam emitter and a co-operating visible or ultraviolet light sensor, arranged to permit the interposition of the moving glass object between them. The sensor is adapted to generate an electrical signal in response to the occurrence of any fluctuation of greater than a predetermined threshold value in the intensity of the received radiation occurring within a predetermined time interval. The emitter may be a laser.

In such apparatus, the sensor normally receives radiation from environmental sources spread over a wide angle. These may include artificial lights placed for general factory illumination, windows, skylights, etc. The result is that the difference in illumination of the sensor caused by the passage of a check amounts to only a small fraction of the total radiant energy being received and registered by the sensor. Thus, the response threshold of the signal generating part of the apparatus has to be set rather low, and this can result in a high level of "false positive" check registrations. Since apparatus of the type in question is normally operatively connected to means for rejecting the glass objects, the apparatus of the prior art above described can reject an undesirably high proportion of such objects. On the other hand, if its response threshold is set high, it will fail to reject genuinely defective glass objects.

It is also known to employ twin phototransistors in conjunction with a push-pull circuit to identify a glass bottle which is maintained stationary in an inspection zone as described in U.S. Pat. No. 3,358,552. In such apparatus, the phototransistors are simultaneously exposed to disparate levels of incident light caused by an identifying surface mark or swirl which magnifies a beam of light. Checks or flaws in the bottle are not detected. The bottle remains stationary while the detector outputs are separately amplified (pushed or pulled) to derive an identification signal.

It is an object of the present invention to provide an improved check detection apparatus including a beam emitter and a co-operating radiation sensor wherein the effective change in received illumination caused by the passage of a check amounts to a large fraction of the total illumination received by the sensor. Another object of the invention is to provide an improved check detection apparatus which, when coupled to a glass object rejecting means, faithfully rejects only defective objects, or at least rejects a higher proportion of defective objects and a lower proportion of sound objects than the apparatus of the prior art.

The invention accordingly provides apparatus for detecting a crack, check or similar flaw in a moving glass object, comprising a visible or ultraviolet light beam emitter and a co-operating spaced apart sensor elements such as that disclosed in co-pending U.S. application 948,179 entitled "Glass Inspection Apparatus" in the name of William Carr assigned to the assignee herein. The moving glass object is interposed between the emitter and the sensor elements. The sensor elements are connected to a difference amplifier and signal processing circuitry which compensates for imbalance in the sensor elements and/or misalignment of the optical components. The difference amplifier and signal processing circuitry cause a signal to be generated in response to the occurrence of any fluctuation of greater than a predetermined threshold value in the intensity of the received radiation occurring within a predetermined time interval.

All movement being relative, "a moving glass object" is to be understood as an object in motion relative to the apparatus.

The predetermined threshold fluctuation in the received radiation intensity, which must be exceeded before a signal is generated, may be found empirically by reference to actual cracks and checks in moving glass objects at a given beam intensity. The threshold value may comprise a fraction or percentage of the "unimpeded" beam intensity and thus be independent of any particular beam intensity.

Once found, the threshold fluctuation can be built into the circuitry of the apparatus, e.g., the circuitry of an amplifier stage which co-operates in generating the signal or in making it effective to reject a glass object. This is done by an appropriate choice of the characteristic values of the relevant circuit components, including the response characteristics of the light sensor, to ensure that a signal is generated only when said threshold fluctuation is exceeded.

The predetermined time interval corresponds substantially to the time taken for the leading edge of the shadow of a crack or check, as cast by the beam shining through the glass object, having shaded one of the sensor elements, to pass on and shade the other sensor element. It is proportional to the spatial separation of the sensor elements and inversely proportional to the speed of travel of said shadow, and may be altered by varying either of those factors. An interval of the order of 1 millisecond is suitable. It will be evident to a skilled person that the chosen interval must be substantially greater than the response time (rise time) of the combined light sensor and amplifier in use, if the apparatus is to function reliably. In addition, the time interval must not be so long as to cause apparent diffusion of the image from the check. In other words, if the speed of rotation of the bottle is very slow, the shadow cast by the check may affect both sensor elements simultaneously or almost simultaneously and thereby seriously affect the resultant signal. The chosen interval is built into the circuitry of the apparatus, again by appropriate choice of the characteristic values of the relevant circuit components, to ensure that a signal is generated only when, the above-mentioned threshold fluctuation having been exceeded, the corresponding shadow passes across the gap between the sensor elements within said interval.

By "the corresponding shadow" is meant the entire illumination sequence during which the threshold fluctuation is established, measured in the direction of travel thereof relative to the sensor. The skilled person will appreciate that shadows thus defined will be of different lengths according to the sharpness or otherwise of the structural discontinuity (in the glass object) giving rise to said shadows. It can be said therefore that, other things being equal, a shadow (a) must not exceed a predetermined length, and (b) must exceed a predetermined intensity differential from start to finish in the direction of travel, if it is to give rise to an effective signal from the apparatus of the invention. The shadow cast by the flaw must not exceed a predetermined length because, to take it to its extreme, if the shadow was of infinite length, there would be no differential illumination and therefore no resultant electric signal. The predetermined intensity is a function of the particular differential diode and associated amplifier used. Each type of differential diode and associated amplifier will require a certain minimum difference in illumination before a useful signal can be generated.

In some embodiments, use may be made of light reflected from a glass object instead of light transmitted therethrough, and the word "shadow" in such cases should, for the purposes of this specification, be given a generous interpretation to include all illumination differentials caused remotely of a glass object in motion, by the passage of a crack or check across a scanning beam directed at said object.

For hollow glass objects, such as bottles and jars, which have an axis of radial symmetry, the required motion of the object is rotation about said axis. The light beam is directed for preference at an interior wall of the hollow glass object, the emitter being introduced through the neck or mouth of the object if necessary. A plurality of emitters and sensors may be arranged for simultaneous scanning of different parts of a glass object.

The generated signal, in a preferred embodiment of the invention, is used to operate a glass object rejection apparatus such as a bottle displacer, which removes faulty objects from a production line.

For the purpose of illustrating the invention, there is shown in the drawings a form which is presently preferred; it being understood, however, that this invention is not limited to the precise arrangements and instrumentalities shown.

FIG. 1 is a cross-section of a glass bottle being inspected by the check detecting apparatus of the present invention.

FIG. 2 is a circuit diagram of a preferred arrangement of the light sensor and difference amplifier.

Figure 3A:
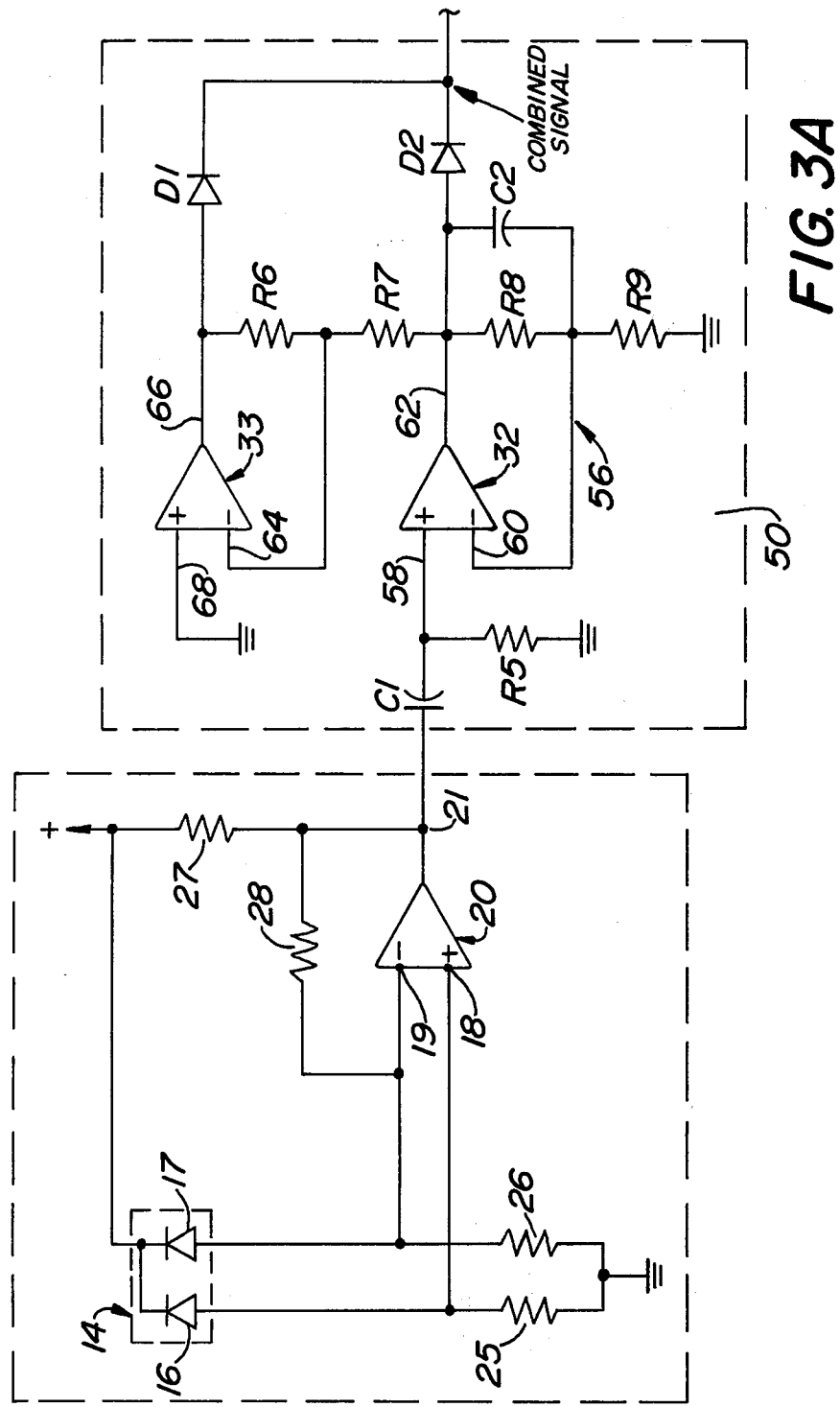
FIGS. 3A and 3B are circuit diagrams of the difference amplifier in FIG. 2 connected to signal processing components of the present invention used to derive the reject signal.

Referring now to the drawings in detail, wherein like numerals indicate like elements, a turntable 1 having a central bottle locating depression 2 supports a freshly molded glass bottle 3 while rotating the bottle about its axis 4. The means for molding the bottle, transporting it to the turntable 1, and removing it therefrom either by acceptance or rejection are all conventional.

A light source 5 and beam-forming devices 6 are mounted in a housing 7 in such fashion that a beam 8 of light produced by this arrangement falls upon an inside wall of the bottle undergoing test. Preferably, the beam is about 10 mm × 1 mm in cross-section.

A second housing 9 containing light-collecting means 10 and a conventional differential photo-diode 11 is mounted in a position wherein it receives a beam 12 comprising part of the light from the original beam 8 as it emerges from passage through the wall of the rotating bottle 3. A horizontal region 13 of the bottle will thus be scanned by the beam 8 in the course of a single revolution thereof, and any irregularities, inclusions (such as "seed", i.e., air bubbles) as well as checks and other cracks will produce a variation in the intensity of the light beam 12 reaching the differential photo-diode 11.

However, only checks or cracks of the type sought produce a variation in intensity of sufficient abruptness to cause the said photo-diode to emit a signal. The rate of change of intensity caused by the passage of a check or a crack through the beam can be regulated by adjusting the speed of revolution of the turntable 1. The appropriate speed, when once found and adjusted, need not subsequently be changed.

The basic signal is produced by the differential photo-diode when a change of illumination, having reached one of the photosensitive resistor elements, reaches the other within a limited time interval such, for example, as 1 millisecond (or 5 milliseconds, or 10). The spatial separation of the photosensitive resistors may be of the order of 50 μm to 2 mm (e.g., 0.5 mm). The required signal as given by the amplifier may be of the order of 1 to 15 volts (e.g., 1.5 volts). Given these parameters, the rise rate of the amplifier should be of the order of 1 to 20 volts per microsecond (e.g., 12 volts per microsecond), and the scanning speed should be of the order of 0.01 m/s to 2 m/s. The scanning speed is the speed at which the shadow of a glass check or flaw passes over the photosensitive resistor elements of the differential diode.

It has already been mentioned that a plurality of light sources and a plurality of differential light sensors may be used simultaneously in inspecting a single vessel. In that event, a rejection signal derived from any differential sensor is sufficient to condemn the vessel being inspected as defective, or to operate a bottle rejection mechanism removing the defective bottle from the production line. When plural light sources are employed, it is preferred that all the light sources be aimed so as to strike an inner wall of the vessel, whereby the emerging light reaches the photo-diode from an outer wall thereof.

Referring specifically to FIG. 2, a differential photo-diode 14 (Siemens, BPX 48) under an applied potential difference of 15 V D.C. from a power source 15, and having photosensitive resistor elements 16, 17 connected "back to back" permits a direct input potential at non-inverting input 18 of difference amplifier 20 and a corresponding input potential at inverting input 19 of amplifier 20. Any potential difference between inputs 18 and 19 will be amplified. The amplifier output 21 is connected to a fixed resistor 22 and a variable limiting resistor 23 by means of which resistors the amplifier gain may be set up. This output may be used to actuate a glass rejection apparatus 40 of known type so that defective glass vessels may be removed in turn from a production line. A preset potentiometer 24 serves, when appropriately adjusted, to eliminate any offset voltage of the whole circuit. A fixed resistor 31 makes potentiometer 24 less sensitive to adjustment. Two input bias resistors 25 and 26 form voltage dividers with the photosensitive resistor elements 16 and 17 respectively for the respective amplifier inputs. Two resistors 28, 26 form a voltage divider to provide negative feedback at 29 to stabilize the amplifier output. A capacitor 30 provides frequency compensation.

The characteristic values or identifying codes of the components mentioned above are:

| Differential diode 14: (Siemens) BPX 48 | | |
|---|---|---|
| Amplifier 20: (R.S. Components Ltd.) TAA 861 | | |
| Resistors: | 25 | 10 KΩ |
| | 26 | 10 KΩ |
| | 27 | 1 KΩ |
| | 28 | 1 MΩ |
| | 22 | 250Ω |
| | 31 | 1.5 MΩ |
| Potentiometers, preset: | | |
| | 24 | 10 KΩ |
| | 23 | 10 KΩ |
| Capacitor: | 30 | 47 pF |

In use, a conventional bottle rejection mechanism 40 is enabled (primed) by the arrival of a bottle on the turntable 1 of FIG. 1. Thereafter, during about 2½ revolutions, a single impulse from the amplifier, indicating the detection of a check in the vessel, activates the rejection mechanism, subsequent impulses (during the standard revolution time) being ignored. Failing a rejection impulse, the vessel is transferred from the turntable to an output line conveyor by conventional means. The next vessel is thereupon fed to the turntable and the inspection cycle repeated.

Figure 3B:
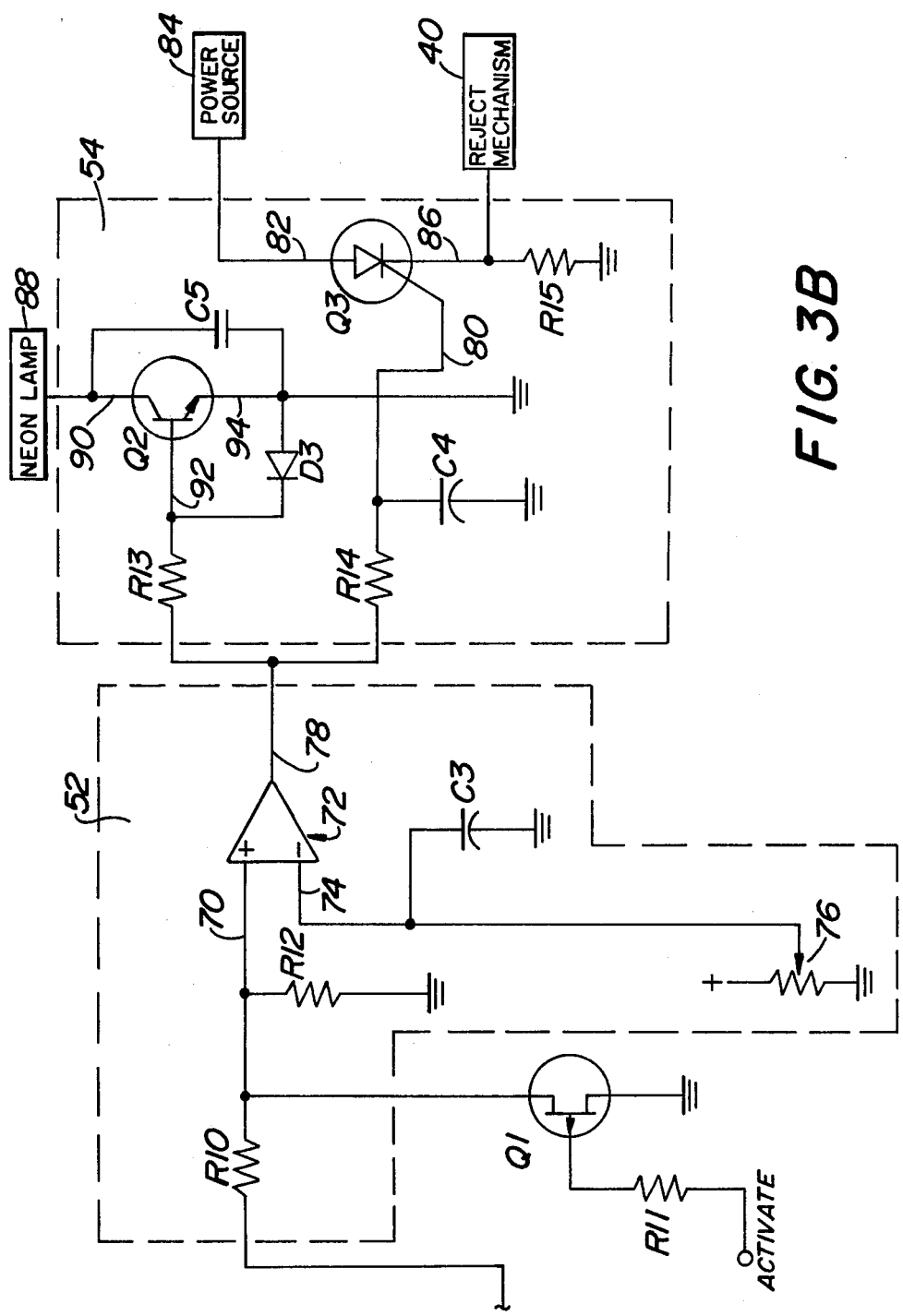

Referring to FIGS. 3A and 3B, there is shown a preferred arrangement for the interconnection of the difference amplifier 20 and the reject mechanism 40 via signal processing circuits 50, 52 and 54 in accordance with the present invention. The preset potentiometer 24 and the resistor 31 have been omitted from the difference amplifier circuit shown in FIG. 3, although the elements may be included if desired. The output 21 of the difference amplifier 20 is capacitor coupled by capacitor C1 to a non-inverting operational amplifier 32 having a negative feedback loop 56 for stabilizing the amplifier gain. The negative feedback loop 56 comprises a resistor R8, capacitor C2, and resistor R9. The loop 56 is connected to the inverting input 60 of operational amplifier 32. The non-inverting input 58 of the amplifier is connected to the capacitor C1 and a resistor R5.

The output 62 of operational amplifier 32 is connected via a resistor R7 to the inverting input 64 of an operational amplifier 33 connected as a unity gain inverting amplifier. The output 66 of operational amplifier 33 is fed back to the inverting input 64 via a resistor R6. The non-inverting input 68 of the operational amplifier is grounded. The output 62 of operational amplifier 32 is rectified by a diode D2. The output 66 of operational amplifier 33 is rectified by a diode D1.

The cathodes of diodes D1 and D2 are connected to rectify and combine the outputs of amplifiers 32 and 33. The combined signal produced at the junction of the diodes is transmitted through the resistor combination R10 and R12 to the non-inverting input 70 of an operational amplifier 72.

The operational amplifier 72 is connected to operate as a comparator. The inverting input 74 of the operational amplifier is connected to a potentiometer 76 which is used to set the threshold value which is to be compared to the combined signal appearing at the non-inverting input 70 of the operational amplifier. A capacitor C3 is connected between ground and the inverting input of the operational amplifier.

The output 78 of the operational amplifier 72 controls the gate 80 of a SCR Q3 via a resistor capacitor combination R14 and C4. The anode 82 of the SCR Q3 is connected to a power source 84 which supplies holding current to the SCR Q3 and which turns the SCR off after a predetermined conduction interval. During the conduction interval, a reject signal is produced at the cathode 86 of SCR Q3 which is resistor coupled to ground by resistor R15. The reject signal operates a conventional reject mechanism 40 which removes a defective bottle from the production line.

The output 78 of operational amplifier 72 also controls the operation of a transistor Q2 via a resistor R13. The transistor Q2 drives a neon lamp 88 connected to the collector 90 of the transistor. A diode D3 is connected between the base 92 and emitter 94 of the transistor. The diode D3 is poled to clamp the base 92 to ground should any negative voltage transients appear at the base. A capacitor C5 couples the collector 90 of transistor Q2 to ground to prevent any switching transient voltage spikes from reaching the neon lamp 88.

Figure 4:
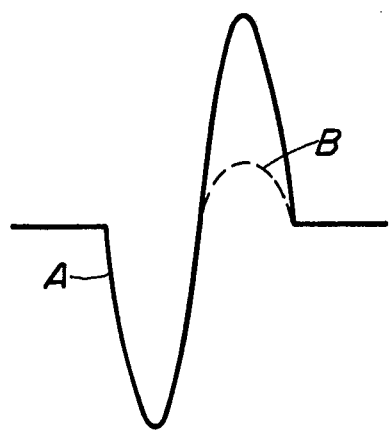
FIG. 4 is a chart of the signal waveforms at certain points of the circuit in FIGS. 3A and 3B.
Figure 4:
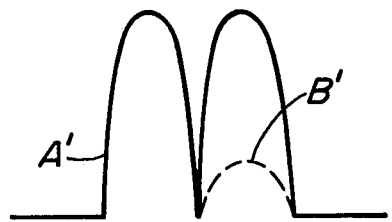
Figure 4:
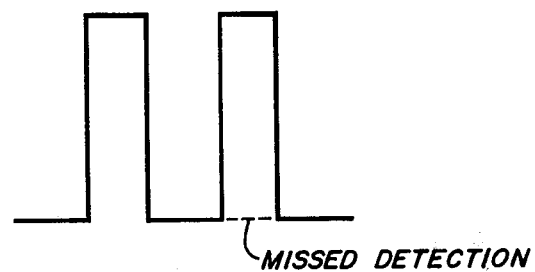

In operation, a check or flaw in region 13 of bottle 3 causes a fluctuation in the intensity of the light beam 12 to be detected sequentially at photosensitive resistors 16 and 17. The difference amplifier 20 produces a signal representative of the difference between the outputs of the photosensitive resistors 16 and 17 as the fluctuations in the intensity of beam 12 are detected. The signal generated at the output 21 of difference amplifier 20 is shown in solid lines in FIG. 4. The output signal is amplified by operational amplifier 32. The output 62 of amplifier 32 is inverted by amplifier 33. The outputs 62 and 66 of amplifiers 32 and 33, respectively, are rectified by diodes D1 and D2, and the combined signal is transmitted to the non-inverting input 70 of amplifier 72. The combined signal at input 70 of amplifier 72 is shown in solid lines in FIG. 4. Each positive going pulse at the non-inverting input 70 will switch the amplifier 72 if the pulse exceeds the threshold voltage set by potentiometer 76. Accordingly, amplifier 72 produces a pair of pulses at its output 78. See FIG. 4. The pulses enable the SCR Q3 to conduct current supplied by power source 84, and the SCR Q3 generates a reject signal at the cathode 86. The pulses appearing at the output 78 of amplifier 72 also switch transistor Q2 on so that the lamp 88 is energized to indicate that a defective bottle has been detected.

If the inverting amplifier 33 and diode D1 are omitted from the circuit, it is possible that an imbalance in the photosensitive resistors 16 and 17 and/or misalignment of the optical components will produce a signal at the output 21 of amplifier 20 which is not sufficiently large to cause the amplifier 72 to switch state. For example, the positive going pulse at the output 21 of amplifier 20 might be a pulse of diminished amplitude B as shown in broken lines in FIG. 4. The amplified pulse B' (pulse B amplified by amplifier 32) is transmitted to the non-inverting input 70 of amplifier 72 but may not be sufficiently strong to switch the amplifier 72, resulting in a missed detection. Accordingly, inverting amplifier 33 and diode D1 are added to the circuit so that the stronger pulse A is recovered by the amplifier 33 and transmitted (as pulse A' at the output of amplifier 33) via diode D1 to the non-inverting input 70 of amplifier 72 together with the diminished pulse B' from amplifier 32 and diode D2. Although pulse B' may not be sufficiently strong to switch the amplifier 72, pulse A' will switch the amplifier. In effect, by adding amplifier 33 and diode D1 to the circuit, two opportunities are provided to trigger a reject signal based on the output of the differential photodiode 14.

The operation of the circuit may be selectively inhibited when a glass bottle 3 is not in position on the table 1. For this purpose, a FET Q1 is connected between ground and the non-inverting input of amplifier 72. The gate of the FET Q1 is controlled by an ACTIVATE signal which may be automatically produced by a microswitch or the like positioned in conventional manner to detect the presence or absence of the bottle 3 on the table 1. Thus, when the bottle 3 is present, the ACTIVATE signal switches the FET Q1 so that the FET does not conduct. When the bottle 3 is absent, the activate signal switches the FET Q1 so that the FET clamps the non-inverting input 70 of amplifier 72 to ground.

Preferred types and values of the components illustrated in FIGS. 3A and 3B are listed in the following table:

| Component | Type/Value |
|---|---|
| 20, 32, 33, 72 | TL082 |
| Q1 | 2N5465 |
| Q2 | MPSA42 |
| Q3 | 2N2324 |
| C1 | 0.33 μF |
| R5 | 470 KΩ |
| R8 | 20 KΩ |
| R9 | 68Ω |
| C2 | 0.01 μF |
| R6, R7 | 22 KΩ |
| D1, D2, D3 | 1N4004 |
| R10, R11 | 10 KΩ |
| R12 | 470 KΩ |
| C3 | 100 μF |
| R13 | 6.8 KΩ |
| R14 | 22 KΩ |
| C4 | 0.01 μF |
| C5 | 0.33 μF |
| R15 | 20Ω |

The present invention may be embodied in other specific forms without departing from the spirit or essential attributes thereof and, accordingly, reference should be made to the appended claims, rather than to the foregoing specification, as indicating the scope of the invention.

I claim:

1. Apparatus for detecting a flaw in a glass bottle, comprising:
   means for directing a light beam at a region of said bottle;
   means for rotating said bottle with respect to said beam to cause said beam to scan said region of said bottle;
   at least two spaced apart sensors disposed to sequentially detect a fluctuation in said light beam as the light beam emerges from said region of said bottle;
   a difference amplifier connected to said sensors for generating a difference signal based on the sequential detection of said fluctuation in intensity of said light beam;
   means for inverting said difference signal;
   means for rectifying said difference signal and the inverted difference signal;
   means for combining the rectified signals; and
   a comparator for detecting whether the combined signal exceeds a predetermined threshold value;
   whereby the passage of a flaw through said beam within a predetermined time interval causes the combining means to generate a combined signal which exceeds said predetermined threshold value, said predetermined time interval being substantially equal to the time taken for the leading edge of a shadow cast by said flaw as said flaw passes through said beam to intercept one of said sensors after having intercepted the other of said sensors.

2. The apparatus according to claim 1 wherein said predetermined threshold value represents a predetermined fraction of the intensity of said beam which is directed to said bottle.

3. The apparatus according to claim 1 wherein said sensors comprise a differential photodiode.

4. A method of detecting a flaw in a glass bottle, comprising:
   directing a light beam at said bottle;
   rotating said bottle with respect to said beam to cause said beam to scan a region of said bottle;
   sequentially detecting a fluctuation in the intensity of said light beam caused by said flaw at first and second locations as said bottle is rotating, said first and second locations being spaced apart from each other and from said bottle;
   generating a difference signal based on the sequential detection of said fluctuation in intensity of said light beam;
   inverting said difference signal;
   rectifying said difference signal and the inverted difference signal;
   combining the rectified signals and comparing the combined signal to a predetermined threshold value;
   generating a reject signal when the combined signal exceeds said predetermined threshold value within a predetermined interval of time substantially equal to the time required to detect said fluctuation at said second location after detecting said fluctuation at said first location.

5. The method according to claim 4 wherein said threshold value represents a predetermined fraction of the intensity of said beam directed to said bottle.

* * * * *